United States Patent
Dunn et al.

(10) Patent No.: US 7,238,698 B2
(45) Date of Patent: Jul. 3, 2007

(54) SUBSTITUTED QUINAZOLINE COMPOUNDS USEFUL AS P38 KINASE INHIBITORS

(75) Inventors: James Patrick Dunn, Los Altos, CA (US); David Michael Goldstein, San Jose, CA (US); Christoph Martin Stahl, Freiburg (DE); Teresa Alejandra Trejo-Martin, Union City, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 477 days.

(21) Appl. No.: 10/824,731

(22) Filed: Apr. 15, 2004

(65) Prior Publication Data

US 2004/0209904 A1    Oct. 21, 2004

Related U.S. Application Data

(60) Provisional application No. 60/463,467, filed on Apr. 16, 2003.

(51) Int. Cl.
  *A61K 31/505*   (2006.01)
  *C07D 239/72*   (2006.01)

(52) U.S. Cl. ............... 514/258.1; 544/242; 544/253; 544/283; 544/292; 514/247; 514/256

(58) Field of Classification Search ............ 544/224, 544/242, 245, 253, 283, 292; 514/247, 256, 514/258
See application file for complete search history.

(56) References Cited

U.S. PATENT DOCUMENTS

| | | | |
|---|---|---|---|
| 5,444,062 A | | 8/1995 | Coe et al. |
| 5,866,572 A | * | 2/1999 | Barker et al. ............ 514/234.5 |
| 5,874,579 A | * | 2/1999 | Henrie II et al. ............ 544/291 |
| 6,399,602 B1 | * | 6/2002 | Barker et al. ............ 514/234.5 |
| 6,476,031 B1 | | 11/2002 | Chakravarty et al. |

FOREIGN PATENT DOCUMENTS

| | | |
|---|---|---|
| EP | 1 052 254 A1 | 11/2000 |
| GB | 1024908 | 4/1966 |
| WO | WO 92/07844 A1 | 5/1992 |

OTHER PUBLICATIONS

Wandel, et al, "P-Glycoprotein and Cytochrome P-450 3A Inhibition: Dissociation of Inhibitory Potencies[1]", Cancer Research, Aug. 15, 1999, pp. 3944-3948, vol. 59:16.
Webb, et al., "Quinazolines as Adenosine Receptor Antagonists: SAR and Selectivity for $A_{2B}$ Receptors", Bioorganic & Medicinal Chemistry, (2003), pp. 77-85, vol. 11.
Hess, et al., "Antihypertensive 2-Amino-4(3H)-quinazolines", Journal of Medicinal Chemistry, (1968), pp. 130-136, vol. 11:1.
Shewchuk, L., et al, "Binding Mode of the 4-Anilinoquinazoline Class of Protein Kinase Inhibitor: X-ray Crystallographic Studies of 4-Anilinoquinazolines Bound to Cyclin-Dependent Kinase 2 and p38 Kinase", J. Med. Chem. 2000, 43:133-138 (XP002293111, compounds 1-3).

* cited by examiner

*Primary Examiner*—Golam M. M. Shameem
(74) *Attorney, Agent, or Firm*—Grant D. Green

(57) ABSTRACT

Compounds having the formula (I),

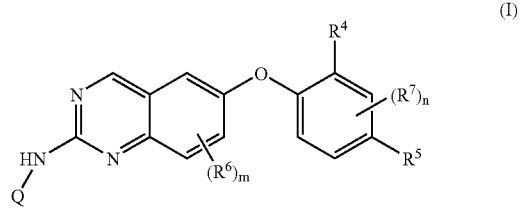

are useful as p38 kinase inhibitors, wherein $R^4$ and $R^5$ are hydrogen, halogen, cyano, haloalkyl, or haloalkoxy, but are not both hydrogen; $R^6$ and $R^7$ are optional substituents, and Q is a non-aromatic moiety as defined in the specification.

18 Claims, No Drawings

SUBSTITUTED QUINAZOLINE COMPOUNDS USEFUL AS P38 KINASE INHIBITORS

RELATED APPLICATIONS

This applications claims priority from U.S. provisional patent application Ser. No. 60/463,467, filed Apr. 16, 2003, incorporated herein by reference in full.

FIELD OF THE INVENTION

The present invention relates to certain quinazoline compounds useful as p38 protein kinase inhibitors. In particular, the present invention relates to 2-amino-6-phenoxy substituted quinazoline compounds, pharmaceutical preparations comprising the same, and methods for using them.

BACKGROUND OF THE INVENTION

Mitogen-activated protein kinases (MAP) are a family of proline-directed serine/threonine kinases that activate their substrates by dual phosphorylation. The kinases are activated by a variety of signals, including nutritional and osmotic stress, UV light, growth factors, endotoxin, and inflammatory cytokines. One group of MAP kinases is the p38 kinase group which includes various isoforms (e.g., p38α, p39β, p38γ and p38δ). The p38 kinases are responsible for phosphorylating and activating transcription factors (as well as other kinases), and are themselves activated by physical and chemical stress, pro-inflammatory cytokines, and bacterial lipopolysaccharide.

More importantly, the products of the p38 phosphorylation have been shown to mediate the production of inflammatory cytokines, including TNF, IL-1, IL-6, and cyclooxygenase-2 (COX-2). Each of these cytokines has been implicated in numerous disease states and conditions. For example, TNF-α is a cytokine produced primarily by activated monocytes and macrophages. Excessive or unregulated production of TNF-α has been implicated as playing a causative role in the pathogenesis of rheumatoid arthritis. More recently, inhibition of TNF production has been shown to have broad application in the treatment of inflammatory conditions, inflammatory bowel disease, Alzheimer's disease, Crohn's disease, multiple sclerosis, and asthma.

Additionally, TNF has been implicated in viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpes virus-7 (HHV-7), human herpes virus-8 (HHV-8), pseudorabies, and rhinotracheitis, among others.

Similarly, IL-1 is produced by activated monocytes and macrophages and plays a role in many pathophysiological responses including rheumatoid arthritis, fever and reduction of bone resorption.

The inhibition of these cytokines by inhibition of the p38 kinase would be beneficial in controlling, reducing and alleviating many of these disease states. p38 MAP kinase inhibitors have demonstrated efficacy in several disease models including arthritis and other joint diseases, sepsis, stroke, myocardial injury, respiratory inflammatory diseases such as chronic obstructive pulmonary disease and asthma, and a wide range of inflammatory conditions. The present invention provides certain 2-amino-6-phenoxy substituted quinazoline compounds useful in inhibiting p38 kinase. U.S. patent application Ser. No. 10/824,980, filed concomitantly herewith and assigned to the present assignee, discloses 2-amino-6-phenoxy substituted 7-aza-quinazoline compounds useful as p38 kinase inhibitors, and the entire contents of said application is hereby incorporated herein by reference.

SUMMARY OF THE INVENTION

The present invention is directed to compounds having the Formula (I):

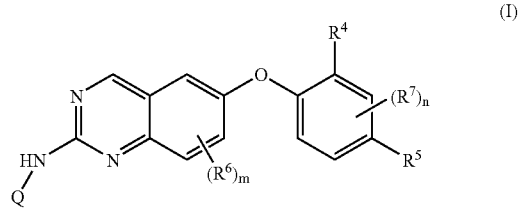

and isomers, prodrugs, and pharmaceutically-acceptable salts thereof, wherein:

Q is —C($R^1R^2R^3$);

$R^1$ is hydrogen, alkyl, hydroxyalkyl, or alkoxyalkyl;

$R^2$ and $R^3$ are selected:
  (i) independently from:
    (a) hydrogen, provided that if $R^1$ is hydrogen, only one of $R^2$ and $R^3$ may be hydrogen;
    (b) alkyl;
    (c) alkyl substituted with one, two, or three of halogen, cyano, —$OR^8$, —$SR^8$, —C(=O)$R^8$, —C(O)$_2R^8$, —C(=O)$NR^8R^9$, —S(O)$_pR^{10}$, —C(O)$_2NR^8R^9$, —S(O)$_2NR^8R^9$, and/or —$NR^8R^9$;
    (d) —$OR^8$, —$SR^8$, —C(=O)$R^8$, —C(O)$_2R^8$, —C(=O)$NR^8R^9$, —S(O)$_pR^{10}$, —C(O)$_2NR^8R^9$, and —S(O)$_2NR^8R^9$;
    (e) cycloalkyl, substituted cycloalkyl, heterocyclyl, substituted heterocyclyl, cycloalkylalkyl, substituted cycloalkylalkyl, heterocycloalkyl, and substituted heterocycloalkyl;
  or alternatively,
  (ii) $R^2$ and $R^3$ are taken together to form an optionally-substituted cycloalkyl or heterocyclyl ring;

$R^4$ and $R^5$ are each independently hydrogen, halogen, cyano, haloalkyl, or haloalkoxy, provided $R^4$ and $R^5$ are not both hydrogen;

$R^6$ may be attached to carbon atoms C5, C7, and/or C8 of the quinazoline ring, and when attached to carbon atom C5 is lower alkyl and when attached to C7 and/or C8 is independently selected from alkyl, halogen, cyano, nitro, hydroxy, alkoxy, haloalkoxy, amino, alkylamino, and alkyl substituted with one to two of halogen, cyano, nitro, hydroxy, alkoxy, haloalkoxy, amino, and/or alkylamino;

$R^7$ is attached to any available carbon atom of the phenyl ring and at each occurrence is independently alkyl, substituted alkyl, halogen, cyano, alkoxy, and haloalkoxy;

$R^8$ and $R^9$ are (i) each independently hydrogen, alkyl, haloalkyl, hydroxyalkyl, alkoxyalkyl, cycloalkyl, substituted cycloalkyl, heterocyclyl, or substituted heterocyclyl; or (ii) when $R^8$ and $R^9$ are attached to the same nitrogen atom (as in —C(O)$_2NR^8R^9$, —S(O)$_2NR^8R^9$, and —$NR^8R^9$), $R^8$ and $R^9$ may be taken together to form an optionally-substituted heterocyclyl ring;

$R^{10}$ is alkyl, hydroxyalkyl, alkoxyalkyl, cycloalkyl, substituted cycloalkyl, heterocyclyl, or substituted heterocyclyl;

m is 0, 1, 2 or 3;
n is 0, 1 or 2; and
p is 1 or 2.

Also provided are pharmaceutical compositions containing at least one compound according to Formula (I), or a pharmaceutically-acceptable salt thereof.

According to another aspect of the invention, there is provided a method of treating a p38-mediated disorder in a patient comprising administering to the patient in need of treatment thereof, a therapeutically-effective amount of at least one compound having the Formula (II):

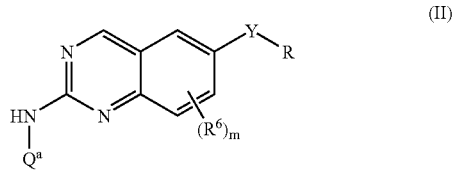

(II)

and/or isomers, prodrugs, and/or pharmaceutically-acceptable salts thereof, wherein:

$Q^a$ is selected from alkyl, substituted alkyl, heteroalkyl, or an optionally-substituted cycloalkyl or heterocyclic ring, provided that Q is not arylalkyl or heteroarylalkyl;

Y is —O—, —S—, or —NR'—, wherein R' is hydrogen, lower alkyl, or lower alkyl substituted with OH;

R is alkyl, substituted alkyl, or optionally-substituted aryl, heteroaryl, cycloalkyl, or heterocyclyl;

$R^6$ may be attached to carbon atoms C5, C7, and/or C8 of the quinazoline ring, and when attached to C5 is lower alkyl and when attached to carbon atoms C7 and/or C8 of the quinazoline ring at each occurrence is independently selected from alkyl, substituted alkyl, halogen, cyano, nitro, hydroxy, alkoxy, haloalkoxy, cycloalkyl, substituted cycloalkyl, heterocyclyl, substituted heterocyclyl, aryl, substituted aryl, heteroaryl, and substituted heteroaryl; and m is 0, 1, 2 or 3.

DETAILED DESCRIPTION OF THE INVENTION

Definitions

The following definitions shall apply in the instant specification and claims, unless otherwise specifically indicated.

As used herein, the term "alkyl" means a linear or branched, saturated monovalent hydrocarbon moiety of one to eight carbon atoms (preferably one to six carbon atoms), e.g., methyl, ethyl, n-propyl, 2-propyl, tert-butyl, pentyl, and the like. "Lower alkyl" means an alkyl of one to four carbon atoms. When a subscript is used herein following a carbon atom, the subscript refers to the number of carbon atoms the named group may contain. Thus, for example, $C_{1-4}$-alkyl means an alkyl of one to four carbon atoms (i.e., lower alkyl) including methyl, ethyl, propyl, iso-propyl, butyl, and tert-butyl.

"Alkylene" means a linear or branched, saturated divalent hydrocarbon moiety of one to eight (preferably one to six) carbon atoms, e.g., methylene, ethylene, propylene, and the like. When reference is made to an alkylene linker group, as in —Y—S(O)$_2$R, —Y—C(O)$_2$NRR, —Y—S(O)$_2$NRR, and so forth, wherein Y is alkylene, it should be understood that the alkylene may be a straight or branched-chain alkylene, and the referenced substituent may be attached to any carbon atom of the alkylene straight or branched chain. Thus, for example, the group —Y—S(O)$_2$R, may include, without limitation, —CH$_2$—S(O)$_2$R, —CH$_2$—CH[S(O)$_2$R]—CH$_3$, —CH$_2$—CH{CH$_2$CH[S(O)$_2$R]CH$_3$}CH$_3$, and so forth.

When the term "alkyl" is used as a suffix following another term, as in "phenylalkyl," or "hydroxyalkyl," this is intended to refer to an alkyl group, as defined above, being substituted with one or more (preferably one) substituent selected from the other, specifically-named group. Thus, "phenylalkyl" includes benzyl, phenylethyl, 2-phenylbutyl, and so forth. "Hydroxyalkyl" includes 2-hydroxyethyl, 1-(hydroxymethyl)-2-methylpropyl, 3,4-dihydroxybutyl, and so forth. Accordingly, as used herein, the term "hydroxyalkyl" is used to define a subset of heteroalkyl groups defined below. In the case of a "substituted cycloalkylalkyl," this is intended to refer to an alkyl group, as defined above, being substituted with one to two substituted cycloalkyl groups, as defined below, and likewise, a "substituted heterocycloalkylalkyl" refers to an alkyl group, as defined above, being substituted with one to two substituted heterocyclyl groups, as defined below.

The term "substituted alkyl" refers to an alkyl group as defined above having one, two, three, or four substituents (preferably one to two), independently selected from the group consisting of halo, haloalkoxy, trifluoromethyl, cyano, nitro, —OR$^a$, —SR$^a$, —S(O)R$^c$, —S(O)$_2$R$^c$, —C(=O)R$^a$, —C(=O)NR$^a$R$^b$, —C(O)$_2$R$^a$, —C(O)$_2$NR$^a$R$^b$, —S(O)$_2$NR$^a$R$^b$, —NR$^a$R$^b$, aryl, substituted aryl, heteroaryl, substituted heteroaryl, cycloalkyl, substituted cycloalkyl, heterocyclyl, and/or substituted heterocyclyl, wherein R$^a$ and R$^b$ are independently selected from hydrogen, $C_{1-6}$-alkyl, aryl, heteroaryl, cycloalkyl, and heterocyclyl, and R$^c$ is selected from $C_{1-6}$-alkyl, aryl, heteroaryl, cycloalkyl, and heterocyclyl, and each of R$^a$, R$^b$, and R$^c$ in turn is optionally substituted with one, two, or three of alkyl, halo, haloalkyl, hydroxy, alkoxy, haloalkoxy, cyano, amino, alkylamino, SO$_2$(alkyl), CO$_2$H, CO$_2$(alkyl), C(=O)H, and/or C(=O) alkyl, and/or a $C_{1-4}$ alkyl substituted with one to two of halo, hydroxy, alkoxy, haloalkoxy, cyano, amino, alkylamino, —SO$_2$(alkyl), CO$_2$H, CO$_2$(alkyl), C(=O)H, and/or C(=O) alkyl.

"Alkoxy" refers to the group OR', wherein R' is alkyl or substituted alkyl. A "lower alkoxy" is a group —OR' wherein R' is $C_{1-4}$alkyl.

"Alkoxycarbonyl" refers to the group COOR', wherein R' is alkyl or substituted alkyl as defined above.

"Alkylsulfonyl" refers to the group —S(O)$_2$R', wherein R' is alkyl or substituted alkyl as defined above.

When the term "oxy" is used as a suffix following another specifically-named group, as in "aryloxy", "heteroaryloxy," or "arylalkyloxy", this means that an oxygen atom is present as a linker to the other, specifically-named group. Thus, for example, "aryloxy" refers to the group —O—R, wherein R is aryl; "heteroaryloxy" refers to the group —O—R', wherein R' is heteroaryl; and "arylalkyloxy" refers to the group —O—R", wherein R" is arylalkyl such as benzyl. Similarly, a "substituted aryloxy" means the group —O—R, wherein R is substituted aryl, and a "substituted heteroaryloxy" means the group —O—R', wherein R' is substituted heteroaryl.

"Amino" refers to the group NH$_2$. Thus, an aminoalkyl refers to an alkyl group having an amino substituent, e.g., —CH$_2$—NH$_2$, —CH$_2$—CH$_2$—NH$_2$, —CH$_2$—CH(NH$_2$)—CH$_3$, and so forth. An alkylamino refers to monoalkylamino groups having the formula —NHR, as well as dialkylamino groups having the formula —NRR, wherein each R is independently alkyl, heterocyclyl, substituted heterocyclyl, cycloalkyl, substituted cycloalkyl, or an alkyl substituted with one to two groups selected from halo, haloalkyl, hydroxy, alkoxy, haloalkoxy, cyano, amino, $SO_2$(alkyl), $CO_2H$, $CO_2$(alkyl), C(=O)H, and/or C(=O)alkyl. Accordingly, an alkylaminoalkyl refers to an alkyl group substituted by one to two of —NHR and/or —NRR, wherein each R is as defined immediately above. A "lower aminoalkyl" refers to a group —NHR' or —NR'R', wherein each R' is $C_{1-4}$alkyl.

When reference is made herein to a carboxmide group —$CO_2$NRR (e.g., as in —$C(O)_2NR^8R^9$), it should be understood this is intended to refer to the group —O—C(=O)—NRR.

The term "aryl" refers to a monovalent, monocyclic or bicyclic moiety in which at least one of the rings is an aromatic, carbocyclic moiety. Thus, the term "aryl" includes phenyl, 1-napthyl, and 2-napthyl. The term "aryl" also includes phenyl rings having fused thereto a second non-aromatic carbocyclic ring, or a heteroaryl or heterocyclic ring such as benzothienyl, benzopyrazolyl, benzopiperadinyl, benzocyclohexyl, and the like, with the understanding, however, that the point of attachment will be to the phenyl ring.

A "substituted aryl" is an aryl group as defined above having one or more (preferably one, two, or three) substituents independently selected from the group consisting of halo, haloalkyl, haloalkoxy, cyano, nitro, —Y—$R^p$, —Y-aryl, —Y-heteroaryl, —Y-cycloalkyl, —Y-heterocyclyl, —Y—$OR^p$, —Y—$NR^pR^q$, —Y—C(=O)$R^p$, —Y—$C(O)_2R^p$, —Y—C(=O)$NR^pR^q$, —Y—$C(O)_2NR^pR^q$, —Y—$S(O)_{0-2}R^p$, —Y—NRS$(O)_2R^q$, —Y—$S(O)_2NR^pR^q$, and/or —Y—NRC(=O)$NR^pR^q$, where Y is absent or a $C_{1-4}$-alkylene group, R is hydrogen, lower alkyl, or hydroxy-$C_{1-4}$ alkyl, and $R^p$ and $R^q$ are independently selected from hydrogen, alkyl, aryl, heteroaryl, cycloalkyl, and heterocyclyl, except when said substituent is —$YS(O)_{1-2}R^p$ or —Y—NRS$(O)_2R^p$, then $R^p$ in these instances is not hydrogen. In each instance, each of $R^p$ and/or $R^q$ in turn is optionally substituted with one to two of alkyl, halo, cyano, hydroxy, alkoxy, amino, alkylamino, haloalkyl, haloalkoxy, hydroxyalkyl, alkoxyalkyl, aminoalkyl, alkylaminoalkyl, —$SO_2$(alkyl), $CO_2H$, $CO_2$(alkyl), C(=O)H, and/or C(=O)alkyl. A preferred group of aryl substituents are those selected from alkyl, haloalkyl, halo, hydroxy, amino, alkylamino, haloalkoxy and alkoxy. Within this group, especially preferred aryl substituents are halo, alkyl, and alkoxy. More specifically, the term "substituted aryl" includes, but is not limited to, fluorophenyl, difluorophenyl, chlorophenyl, methoxyphenyl, and the like.

The term "carbocyclic" means a cyclic moiety in which all ring atoms are carbon atoms, including saturated, partially unsaturated, and unsaturated rings.

The term "cycloalkyl" as used herein refers to saturated or partially unsaturated, monovalent, monocyclic carbocyclic moieties of three to seven ring carbon atoms and further includes such rings having a carbon-carbon bridge of one, two, or three bridgehead carbon atoms, and/or having a second ring fused thereto, with the understanding that said second fused ring may be a non-aromatic carbocyclic or heterocyclic ring in which case the point of attachment will be to the non-aromatic carbocyclic ring moiety. Thus, the term "cycloalkyl" includes such rings as cyclopropyl, cyclopentyl, cyclopentenyl, cyclohexyl, cyclohexenyl, and the like. Additionally, one or two carbon atoms of a cycloalkyl group may optionally contain a carbonyl oxygen group, e.g., one or two atoms in the ring may be a moiety of the formula —C(=O)—.

A "substituted cycloalkyl" is a cycloalkyl group as defined above having one, two, or three substituents independently selected from the group consisting of halo, haloalkyl, haloalkoxy, cyano, nitro, —Y—$R^s$, —Y-cycloalkyl, —Y-heterocyclyl, —Y—$OR^s$, —Y—$NR^sR^t$, —Y—C(=O)$R^s$, —Y—$C(O)_2R^s$, —Y—C(=O)$NR^sR^t$, —Y—$C(O)_2NR^sR^t$, —Y—$S(O)_{0-2}R^s$, —Y—NRS$(O)_2R^s$, Y—$S(O)_2NR^sR^t$, and/or —Y—NRC(=O)$NR^sR^t$, wherein Y is absent or a $C_{1-4}$alkylene group, R is hydrogen, lower alkyl, or hydroxy$C_{1-4}$alkyl, and $R^s$ and $R^t$ are independently selected from hydrogen, alkyl, cycloalkyl, and heterocyclyl, except when said substituent is —$YS(O)_{1-2}R^s$ or —Y—NRS$(O)_2R^s$, then $R^s$ in these instances is not hydrogen. In each instance, each of $R^s$ and/or $R^t$ in turn is optionally substituted with one to two of lower alkyl, halo, cyano, hydroxy, alkoxy, amino, alkylamino, haloalkyl, haloalkoxy, hydroxyalkyl, alkoxyalkyl, aminoalkyl, alkylaminoalkyl, —$SO_2$(alkyl), $CO_2H$, $CO_2$(alkyl), C(=O)H, and/or C(=O)alkyl. Preferred substituents for substituted cycloalkyl groups include -(alkylene)$_n$-hydroxy, -(alkylene)$_n$-lower alkoxy, -(alkylene)$_n$-S$(O)_2$(lower alkyl), and -(alkylene)$_n$-$CO_2$(lower alkyl), where n is 0, 1, or 2.

The term "halo," "halide" or "halogen," when referring to a substituent means fluoro, chloro, bromo, or iodo (preferably fluoro or chloro).

The term "haloalkyl" means alkyl substituted with one or more same or different halo atoms, e.g., —$CH_2Cl$, —$CF_3$, —$CH_2CF_3$, —$CH_2CCl_3$, and the like, and further includes those alkyl groups such as perfluoroalkyl in which all alkyl hydrogen atoms are replaced by fluorine atoms.

The term "haloalkoxy" means a haloalkyl group as defined above linked through an oxygen atom, e.g., it includes —O—$CH_2Cl$, —O—$CF_3$, —O—$CH_2CF_3$, —O—$CH_2CCl_3$, and the like.

The term "heteroalkyl" as used herein means an alkyl moiety defined above, wherein one, two or three hydrogen atoms have been replaced with a substituent independently selected from the group consisting of —$OR^d$, —$NR^dR^e$, and $S(O)_nR^d$ (where n is an integer from 0 to 2), with the understanding that the point of attachment of the heteroalkyl moiety is through a carbon atom, wherein $R^d$ and $R^e$ are selected from hydrogen, alkyl, substituted alkyl (but not including arylalkyl or heteroarylalkyl), cycloalkyl, substituted cycloalkyl, heterocyclyl, and substituted heterocyclyl, except when $R^d$ is attached to $S(O)_nR^d$ and n is 1 or 2, then $R^d$ is not hydrogen. Additionally, when $R^d$ and $R^e$ are attached to the same nitrogen atom, they may be taken together to form an optionally-substituted heterocyclyl or heteroaryl ring. Representative examples include, but are not limited to, 2-hydroxyethyl, 3-hydroxypropyl, 2-hydroxymethylethyl, 2,3-dihydroxypropyl, 1-hydroxymethylethyl, 3-hydroxybutyl, 2,3-dihydroxybutyl, 2-hydroxy-1-methylpropyl, 2-amino-ethyl, 3-aminopropyl, 2-methylsulfonylethyl, aminosulfonylmethyl, aminosulfonylethyl, methylaminosulfonylmethyl, methylaminosulfonylethyl, methylaminosulfonylpropyl, 2-hydroxyethyl, 3-hydroxypropyl, 2-hydroxymethylethyl, 2,3-dihydroxypropyl, and so forth.

"Heterocyclyl," "heterocyclyl," or "heterocyclic" refers to a saturated or partially-unsaturated non-aromatic monocyclic or bicyclic moiety in which one or two ring atoms are heteroatoms selected from N, O, or $S(O)_n$ (where n is an integer from 0 to 2), the remaining ring atoms being carbon atoms, and additionally, one or two carbon atoms may optionally contain a carbonyl oxygen group, e.g., one or two atoms in the ring may be a moiety of the formula —C(=O)—. Thus, the term heterocyclyl includes rings such as tetrahydropyranyl, tetrahydrofuryl, piperidinyl, piperazinyl, morpholinyl, pyrrolidinyl, pyrrolinyl, imidazolidinyl, imidazolinyl, and the like. In the case of a bicyclic heterocyclyl, one of the two rings may be a non-aromatic carbocyclic with the point of attachment, however, being to the heterocyclic ring.

A "substituted heterocyclyl" or "substituted heterocycle" refers to a heterocyclyl group as defined above having one, two, or three substituents (preferably one to two substituents) selected from the group consisting of halo, haloalkyl, haloalkoxy, cyano, nitro, —Y—$R^s$, —Y-cycloalkyl, —Y-heterocyclyl, —Y—$OR^s$, —Y—$NR^sR^t$, —Y—C(=O)$R^s$, —Y—C(O)$_2R^s$, —Y—C(=O)$NR^sR^t$, —Y—C(O)$_2NR^sR^t$, —Y—S(O)$_{0-2}R^s$, —Y—NRS(O)$_2R^s$, —Y—S(O)$_2NR^sR^t$, and/or —Y—NRC(=O)$NR^sR^t$, wherein Y, R, $R^s$ and $R^t$ are as defined above for substituted cycloalkyl groups, such that $R^s$ and $R^t$ are, in turn, at each instance independently optionally substituted with one to two further groups as recited above in the definition for substituted cycloalkyl. Preferred substituents for substituted heterocyclyl groups include -(alkylene)$_n$-hydroxy, -(alkylene)$_n$-lower alkoxy, -(alkylene)$_n$-S(O)$_2$(lower alkyl), and -(alkylene)$_n$-CO$_2$ (lower alkyl), where n is 0, 1, or 2.

"Heteroaryl" means a monovalent, monocyclic aromatic moiety of 5 to 6 ring atoms containing one, two, three, or four ring heteroatoms, each independently selected from N, O, or S, the remaining ring atoms being carbon, and it also includes such rings having a second ring fused thereto of five to six ring atoms, wherein the second fused ring may be aromatic or nonaromatic and may be carbocyclic, heterocyclic, or a heteroaryl ring, with the understanding, however, that in such cases the point of attachment will be to an aromatic ring containing at least one heteroatom. Thus, the term heteroaryl includes, but is not limited to, pyridyl, furyl, thiophenyl, thiazolyl, isothiazolyl, triazolyl, imidazolyl, isoxazolyl, pyrrolyl, pyrazolyl, pyrimidinyl, benzofuryl, isobenzofuryl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and derivatives thereof.

A "substituted heteroaryl" is a heteroaryl ring as defined above having one, two or three (preferably one or two) substituents selected from the group consisting of halo, haloalkyl, haloalkoxy, cyano, nitro, —Y—$R^p$, —Y-aryl, —Y-heteroaryl, —Y-cycloalkyl, —Y-heterocyclyl, —Y—$OR^p$, —Y—$NR^pR^q$, —Y—C(=O)$R^p$, —Y—C(O)$_2R^p$, —Y—C(=O)$NR^pR^q$, —Y—C(O)$_2NR^pR^q$, —Y—S(O)$_{0-2}R^p$, —Y—NRS(O)$_2R^q$, —Y—S(O)$_2NR^pR^q$, and/or —Y—NRC(=O)$NR^pR^q$, wherein Y, R, $R^p$ and $R^q$ are as defined above for substituted aryl groups, such that $R^p$ and $R^q$ are, in turn, at each instance independently optionally substituted with one to two further substituents as recited above in the definition for substituted aryl. Preferred substituents for substituted heteroaryl groups include alkyl, haloalkyl, heterocyclyl, halo, nitro, cyano, and -(alkylene)$_n$-CO$_2$R (where n is 0 or 1 and R is hydrogen or alkyl).

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optional" or "optionally" means that the subsequently described event may but need not occur, and it includes instances where the event occurs and instances in which it does not. For example, "optionally-substituted cycloalkyl" refers to both cycloalkyl groups and substituted cycloalkyl groups, as defined above. When the term "optionally-substituted" precedes a number of different types of rings in one line or string, e.g., as in "optionally-substituted cycloalkyl or heterocyclyl," or "optionally-substituted carbocyclic or heterocyclic ring," or "optionally-substituted aryl, heteroaryl, cycloalkyl, or heterocyclyl," it is intended that the term "optionally-substituted" modifies each of the rings identified in the line or string.

When the term "optionally-substituted" is used with respect to a particularly-named cyclic group, such as "optionally-substituted cyclohexyl," or "optionally-substituted piperidinyl," it should be understood that the optional substituents for such particularly-named rings may be selected from the group of substituents recited above with respect to which the genus of which the particularly-named group is a member. Thus, for example, an "optionally-substituted cyclohexyl" may be an unsubstituted cyclohexyl or a cyclohexyl group having one, two, or three substituents selected from those recited above for substituted cycloalkyl.

When reference is made herein to the C5, C7, or C8 carbon atoms of the quinazoline ring, the numbering of the ring atoms is intended to be as follows:

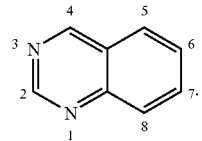

"Pharmaceutically acceptable excipient" means an excipient that is useful in preparing a pharmaceutical composition that is generally safe, non-toxic and neither biologically nor otherwise undesirable. The term includes excipients that are acceptable for veterinary use as well as human pharmaceutical use. A "pharmaceutically acceptable excipient" as used in the specification and claims includes both one and more than one such excipient.

"Pharmaceutically acceptable salt" of a compound means a salt that is generally safe, non-toxic and neither biologically nor otherwise undesirable, and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 4,4'-methylenebis-(3-hydroxy-2-ene-1-carboxylic acid), 3-phenylpropionic acid, trimethylacetic acid, tertiary butyl-acetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanol-amine, triethanolamine, N-methylglucamine, and the like.

The terms "pro-drug" and "prodrug" are used interchangeably herein and refer to any compound which releases an active parent drug according to Formula I or II in vivo when such prodrug is administered to a mammalian subject. Prodrugs of a compound of Formula I or II are prepared by modifying one or more functional group(s) present in the compound of Formula I or II in such a way that the modification(s) may be cleaved in vivo to release the parent compound. Prodrugs include compounds of Formula I or II wherein a hydroxy, amino, or sulfhydryl group in a compound of Formula I or II is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-di-methylaminocarbonyl) or hydroxy functional groups in compounds of Formula I or II, and the like.

"Protecting group" refers to an atom or group of atoms that is attached to a reactive group in a molecule and masks, reduces, or prevents the reactivity of the group to which it is attached. Examples of protecting groups can be found in Green and Wuts, *Protective Groups in Organic Chemistry* (Wiley, 2nd ed. 1991), and Harrison and Harrison et al., *Compendium of Synthetic Organic Methods*, Vols. 1-8 (John Wiley and Sons, 1971-1996). Representative amino protecting groups include formyl, acetyl, trifluoroacetyl, benzyl, benzyloxycarbonyl (CBZ), tert-butoxy-carbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as with benzyl or lower alkyl and trityl ethers as well as alkyl ethers, tetrahydropyranyl ethers, trialkylsilyl ethers, and allyl ethers.

"Treating" or "treatment" of a disease includes: (1) preventing the disease, i.e., causing the clinical symptoms of the disease not to develop in a mammal that may be exposed to or pre-disposed to the disease but does not yet experience or display symptoms of the disease; (2) inhibiting the progression of the disease, i.e., arresting or reducing the development of the disease or its symptoms; and (3) relieving the disease, i.e., causing regression of the disease or its symptoms.

"A therapeutically effective amount" means the amount of a compound that, when administered to a mammal for treating a disease, is sufficient to effect a treatment for the disease. The "therapeutically effective amount" will vary depending on such factors as the compound being administered, the type of disease being treated, the progression or severity of the disease state, and the age, weight, and general health of the mammal being treated.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers," and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the (R) and (S) sequencing rules of Cahn and Prelog, or by the manner in which the molecule rotates the plane of polarized light and designated as dextrorotatory or levorotatory (i.e., as (+) or (−)-isomers respectively). A chiral compound can exist as either an individual enantiomer or as a mixture thereof. A mixture containing different enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures (racemic or otherwise) thereof. The methods for the determination of stereochemistry and the separation of stereoisomers are well-known in the art (see March, *Advanced Organic Chemistry*, Chap. 4, 4th edition, John Wiley and Sons, New York [1992]).

PREFERRED EMBODIMENTES

While the definition of this invention is set forth in the Summary of the Invention, certain compounds of Formula (D) are preferred.

Preferred compounds according to the invention are those having Formula (Ip),

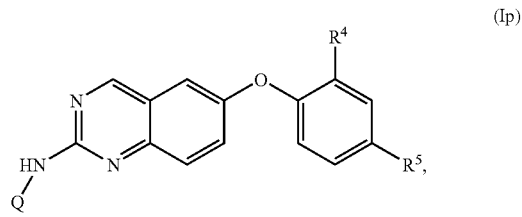

(Ip)

and isomers, prodrugs, and pharmaceutically-acceptable salts thereof, wherein:

Q is —C($R^1R^2R^3$);

$R^1$ is selected from hydrogen, alkyl, hydroxyalkyl, and alkoxyalkyl;

$R^2$ and $R^3$ are (i) independently selected from alkyl, cycloalkyl, substituted cycloalkyl, heterocyclyl, substituted heterocyclyl, and alkyl substituted with one, two or three of —$OR^8$, —$SR^8$, —$S(O)_pR^{10}$, —$C(O)_2R^8$, cycloalkyl, substituted cycloalkyl, heterocyclyl, and/or substituted heterocyclyl; or (ii) $R^2$ and $R^3$ are taken together to form an optionally-substituted non-aromatic carbocyclic or heterocyclic ring;

$R^4$ and $R^5$ are halogen, cyano, trifluoromethyl, or trifluoromethoxy;

$R^8$ and $R^9$ are independently selected from hydrogen, alkyl, hydroxyalkyl, alkoxyalkyl, cycloalkyl, substituted cycloalkyl, heterocyclyl, and substituted heterocyclyl;

$R^{10}$ is alkyl, cycloalkyl, substituted cycloalkyl, heterocyclyl, or substituted heterocyclyl; and p is 1 or 2.

More preferred are compounds of Formula (Ip) as immediately defined above, wherein $R^1$ is selected from hydrogen and $C_{1-4}$alkyl;

$R^2$ and $R^3$ are (i) independently selected from hydrogen, $C_{1-6}$alkyl, and $C_{1-6}$alkyl substituted with hydroxy, —O($C_{1-4}$alkyl), or —$S(O)_2$($C_{1-4}$alkyl); or (ii) $R^2$ and $R^3$ taken together form a $C_{3-7}$cycloalkyl or a five to six membered monocyclic heterocyclic ring, wherein each of said rings is optionally-substituted with up to one of $R^{12}$ and/or up to one of $R^{14}$;

$R^4$ and $R^5$ are both halogen; and $R^{12}$ and $R^{14}$ are independently selected from $C_{1-4}$alkyl, hydroxy, oxo (=O), —O($C_{1-4}$alkyl), —C(=O)H, —C(=O)($C_{1-4}$alkyl), —C(O)$_2$H, —C(O)$_2$($C_{1-4}$alkyl), and —S(O)$_2$($C_{1-4}$alkyl).

In compounds of Formulae (I) and (Ip), preferred compounds are those compounds wherein $R^1$ is selected from hydrogen and $C_{1-4}$alkyl.

In compounds of Formula (I) and (Ip), preferred compounds are those wherein one of $R^2$ and $R^3$ is selected from alkyl substituted with one, two or three of —OR$^8$, —SR$^8$, —C(=O)R$^8$, —C(O)$_2$R, —C(=O)NR$^8$R$^9$, —S(O)$_p$R$^{10}$, —C(O)$_2$NR$^8$R$^9$, —S(O)$_2$NR$^8$R$^9$, cycloalkyl, substituted cycloalkyl, heterocyclyl, and/or substituted heterocyclyl (wherein $R^8$ and $R^9$ are independently selected from alkyl, hydroxyalkyl, alkoxyalkyl, cycloalkyl, substituted cycloalkyl, heterocyclyl, and substituted heterocyclyl). A more preferred group of compounds are those wherein $R^2$ and $R^3$ are selected from alkyl, hydroxyalkyl, alkoxyalkyl, —($C_{1-4}$alkylene)-S(O)$_p$R$^{10}$, and —($C_{1-4}$alkylene)-C(O)$_2$R$^8$ (wherein $R^8$ and $R^{10}$ are lower alkyl). Also preferred are those compounds wherein $R^2$ and $R^3$ are taken together to form an optionally-substituted $C_{3-7}$cycloalkyl or an optionally-substituted heterocyclic ring. Within this group of preferred compounds, more preferred are those compounds wherein $R^2$ and $R^3$ are taken together to form optionally-substituted cyclohexyl, piperidin-4-yl, or tetrahydropyran-4-yl. Preferably, said cycloalkyl and heterocyclic groups formed by $R^2$ and $R^3$ are unsubstituted or substituted with OH, —O($C_{1-4}$alkyl), —C(O)$_2$($C_{1-4}$alkyl) and/or —S(O)$_2$ ($C_{1-4}$alkyl), more preferably with one of —C(O)$_2$(Et) or —S(O)$_2$(CH$_3$).

In compounds of Formula (I) and (Ip), preferably $R^4$ and $R^5$ are both halogen. More preferred compounds are those wherein $R^4$ and $R^5$ are both fluoro.

Still further, combinations of the preferred groups described herein form other preferred embodiments. In this manner, a variety of preferred compounds are embodied within the present invention.

Another group of preferred compounds are those having the formula,

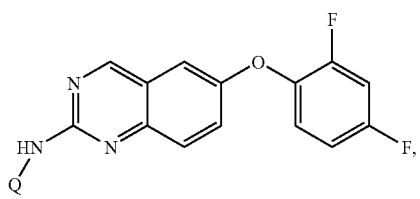

wherein Q is —C(R$^1$R$^2$R$^3$); $R^1$ is selected from hydrogen, alkyl, hydroxyalkyl, and alkoxyalkyl; and $R^2$ and $R^3$ are (i) independently selected from hydrogen, alkyl, cycloalkyl, substituted cycloalkyl, heterocyclyl, substituted heterocyclyl, and $C_{1-6}$alkyl substituted with one or two of —OR$^8$, —SR$^8$, —S(O)$_p$R$^{10}$, —C(O)$_2$R$^8$, —NR$^8$R$^9$, cycloalkyl, substituted cycloalkyl, heterocyclyl and/or substituted heterocyclyl; or (ii) $R^2$ and $R^3$ are taken together to form an optionally-substituted non-aromatic carbocyclic or heterocyclic ring.

Another group of preferred compounds are those having the formula:

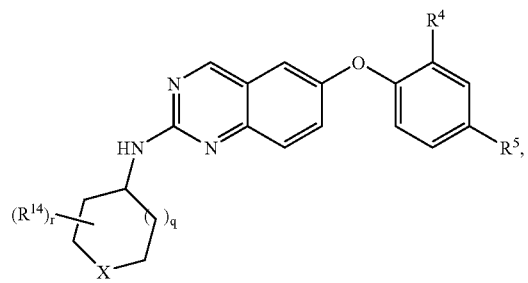

wherein:
$R^4$ and $R^5$ are both halogen (more preferably fluoro);
X is —O—, —C(=O)—, —N(R$^{12a}$)—, or —CH(R$^{12b}$)—;
$R^{12a}$ is selected from hydrogen, $C_{1-4}$alkyl, —C(=O)R$^{15}$, —C(O)$_2$R$^{15}$, and —S(O)$_2$($C_{1-4}$alkyl);
$R^{12b}$ is selected from hydrogen, $C_{1-4}$alkyl, —OR$^{15}$, —C(=O)R$^{15}$, —C(O)$_2$R$^{15}$, and —S(O)$_2$($C_{1-4}$alkyl);
$R^{14}$ is selected from $C_{1-4}$alkyl, hydroxy, oxo (=O), —OR$^{15}$, —C(=O)R$^{15}$, —C(O)$_2$R$^{15}$, and —S(O)$_2$C$_{1-4}$alkyl);
$R^{15}$ is selected from hydrogen and $C_{1-4}$alkyl;
q is 0 or 1; and
r is 0 or 1.

Even more preferred are compounds as immediately defined above, wherein X is —NR$^{12a}$—, $R^{12a}$ is S(O)$_2$(C$_{1-4}$alkyl), q is 1, and r is 0.

Utility

Compounds of Formulae I and II are useful for the treatment of any disorder or disease state in a human, or other mammal, which is exacerbated or caused by excessive or unregulated proinflammatory cytokines (i.e., TNF, IL-1, etc.), or p38 kinase activation by such mammal. Compounds of Formulae I and II inhibit p38 kinase in in vitro assays and inhibit TNF-α or IL-1B release in cell based assays.

In view of their activity as inhibitors of p38kinase, the compounds of the invention are useful for treating inflammatory diseases, autoimmune diseases, destructive bone disorders, proliferative disorders, angiogenic disorders, infectious diseases, neurodegenerative diseases, and viral diseases. Compounds of the invention are useful in treating arthritis, including but not limited to rheumatoid arthritis, spondylitis, gouty arthritis, osteoarthritis, systemic lupus erythematosus (SLE), juvenile arthritis, and other arthritic conditions. In addition, compounds of the present invention are useful in treating pulmonary disorders or lung inflammation, including adult respiratory distress syndrome, pulmonary sarcoidosis, asthma, silicosis, and chronic obstructive pulmonary disease. Furthermore, compounds of the present invention are useful in treating viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. Moreover, compounds of the present invention are useful in the treatment of bone resorption diseases, such as osteoporosis, endotoxic shock, toxic shock syndrome, reperfusion injury, autoimmune disease including graft vs. host reaction and allograft rejections, cardiovascular diseases including myocardial infarction, atherosclerosis, thrombosis, congestive heart failure, cardiac reperfusion injury, renal reperfusion injury, liver disease and nephritis, and myalgias due to infection.

The compounds of the present invention are also useful for the treatment of influenza, diabetes, systemic lupus erthrematosis (SLE), skin-related conditions such as psoriasis, eczema, burns, dermatitis, keloid formation, and scar tissue formation. Compounds of the present invention are also useful in treating gastrointestinal conditions such as inflammatory bowel disease, Crohn's disease, gastritis, irritable bowel syndrome, and ulcerative colitis. The compounds of the present invention can also be used in treating ophthalmic diseases, such as retinitis, retinopathies, uveitis, ocular photophobia, and acute injury to the eye tissue. Compounds of the invention also would be useful for treatment of cancer and angiogenesis, including neoplasia and metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant conditions such as hemangiomas, including infantile hemangiomas, angiofibroma of the nasopharynx and avascular necrosis of bone; diabetic nephropathy and cardiomyopathy; and disorders of the female reproductive system such as endometriosis.

The compounds of the present invention are also useful in treating central nervous system disorders, such as Alzheimer's disease, multiple sclerosis, and depression.

In addition, compounds of the present invention are also useful for preventing the production of cyclooxygenase-2 and thus are useful in treating those diseases responsive to inhibition of COX-2, such as fever, edema, and pain, including headache, neuromuscular pain, dental pain, arthritic pain and pain caused by cancer.

Besides being useful for human treatment, compounds of the present invention are also useful for veterinary treatment of animals such as companion, exotic, and farm animals, including mammals, rodents, and the like. More preferred animals include horses, dogs, and cats.

Furthermore, compounds of the present invention can be used in co-therapies, partially or completely, in place of other conventional antiinflammatory agents, such as together with steroids, cyclooxygenase-2 inhibitors, NSAIDs, aspirin, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention. When reference herein is made generally to "TNF" inhibition, this is intended to encompass both TNF-α and TNF-β inhibition, unless specifically delineated otherwise.

Abbreviations

For ease of reference, the following abbreviations are used in the general synthetic schemes and Examples below:
EtOH=ethanol
MeOH=methanol
EtOAc=ethyl acetate
DCE=1,2-dichloroethane
DCM=dichloromethane
DMF=dimethylformamide
NaOH=sodium hydroxide
NMP=1-methyl-2-pyrrolidinone
TEA or $Et_3N$=triethylamine
TFA=trifluoroacetic acid
THF=tetrahydrofuran
Mp=melting point
MW=molecular weight
h=hour(s)
rt.=room temperature General Synthetic Schemes The compounds of the present invention can be prepared in a number of ways known to one skilled in the art. Preferred methods include, but are not limited to, the general synthetic procedures described below. These schemes are merely illustrative. Various modifications to these schemes can be made and will be apparent to one skilled in the art.

The starting materials and reagents used are either available from commercial suppliers such as Aldrich Chemical Co. (Milwaukee, Wis., USA), Bachem (Torrance, Calif., USA), Enika Chemie or Sigma (St. Louis, Mo., USA), Maybridge (Dist: Ryan Scientific, P.O. Box 6496, Columbia, S.C. 92960), etc.; or they can be prepared by methods known to those skilled in the art following procedures set forth in the literature. The starting materials and the intermediates of the reaction may be isolated and purified if desired using conventional techniques, including but not limited to filtration, distillation, crystallization, chromatography, and the like. Such materials may be characterized using conventional means, including physical constants and spectral data. In the Schemes, the variables Q, $R^1$, $R^2$, $R^3$, $R^4$, $R^5$, $R^6$, etc., are defined as set forth in the Summary of Invention and claims.

General Scheme 1:

-continued

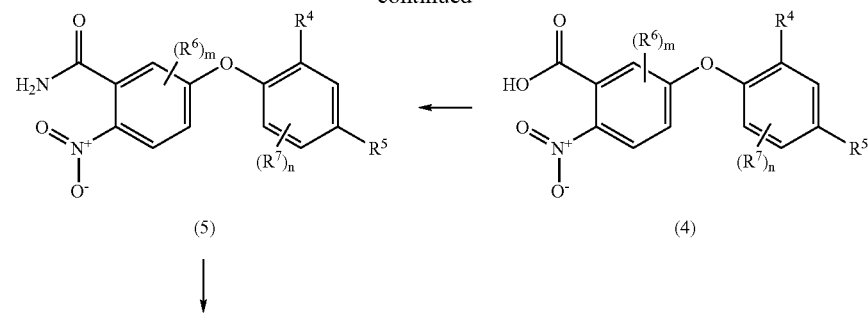

(5)    (4)

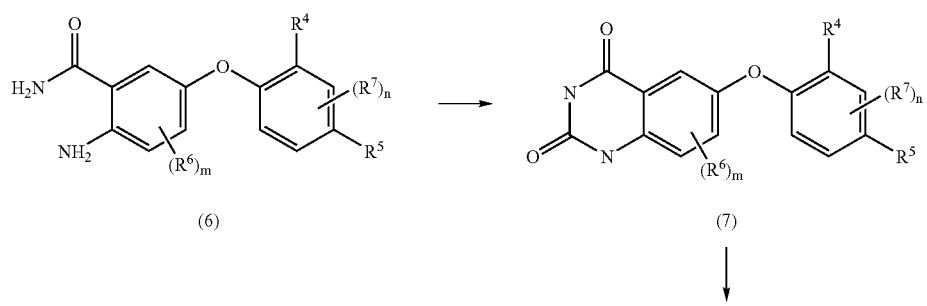

(6)    (7)

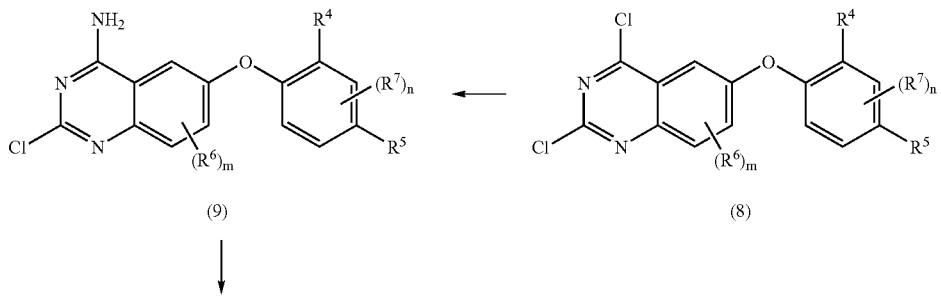

(9)    (8)

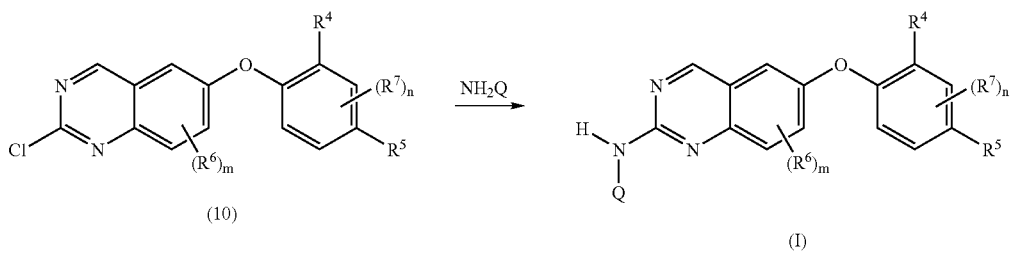

(10)    (I)

Methyl 5-chloro-2-nitrobenzoate (1) is reacted with an appropriately-substituted phenol (2) and base such as potassium carbonate in a solvent such as NMP to form the corresponding phenoxy-2-nitro-benzoic acid methyl ester (3). Compound (3) is hydrolyzed upon treatment with basic solution such as NaOH in water/MeOH to provide benzoic acid (4). Benzoic acid (4) is treated with thionyl chloride in solvent such as DMF to provide an intermediate acid chloride, which upon treatment with NH$_4$OH in solvent such as THF provides benzamide (5). The nitro-benzamide (5) can be hydrogenated in solvent such as EtOH to provide amino-benzamide (6).

Amino-benzamide (6) can be cyclized to provide quinazoline-2,4-dione (7) upon treatment with urea in solvent such as NMP. Compound (7) can be treated with N,N-diethylaniline and POCl$_3$ to give 2,4-dichloroquinazoline (8), which, when treated with NH$_3$ in a solvent such as MeOH provides compound (9). Compound (9) can be reacted with t-butyl nitrite in THF to provide compound (10) which, when coupled with an appropriate amine NH$_2$Q, e.g., in NMP, affords compounds of Formula (I).

General Scheme 2:

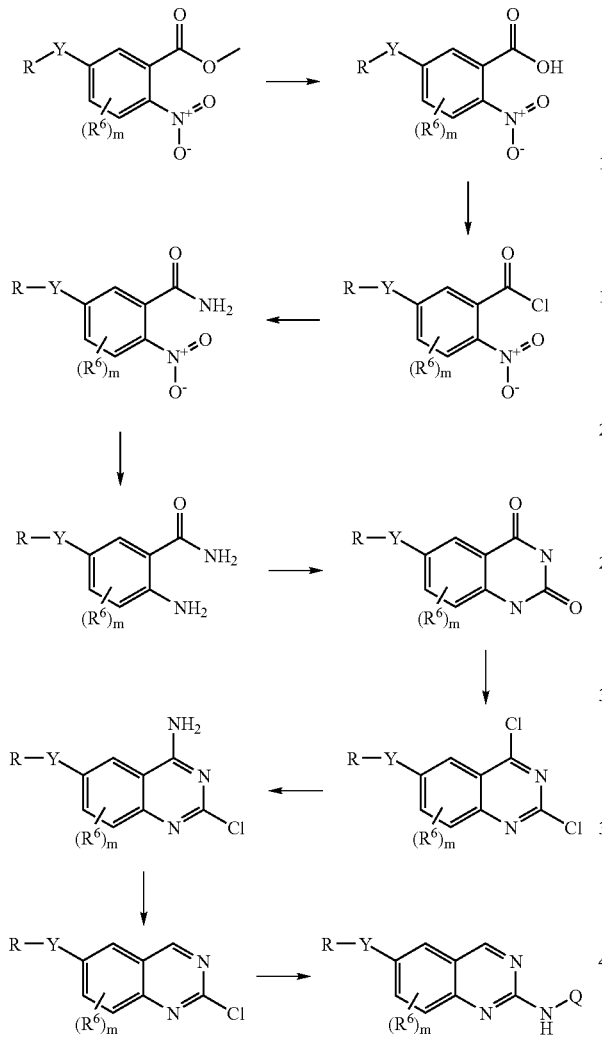

Compounds having formula (II) are prepared as shown in Scheme 2, following the same general methodology as described above for Scheme 1.

EXAMPLE 1

2-[6-(2,4-Difluoro-phenoxy)-quinazolin-2-ylamino]-2-ethyl-propane-1,3-diol

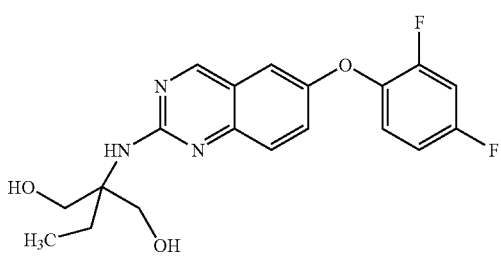

1A. 5-(2,4-Difluoro-phenoxy)-2-nitro-benzoic acid methyl ester

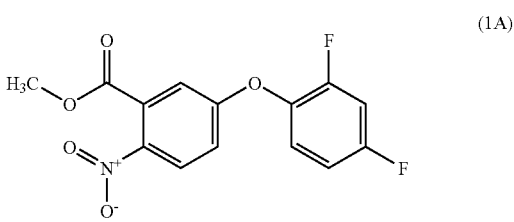

(1A)

Methyl 5-chloro-2-nitrobenzoate (73 g, 0.34 mol), 2,4-difluorophenol (51.1 g, 0.39 mol) and potassium carbonate (73 g, 0.53 mol) in NMP (200 mL) were stirred at 160° C. for 2 h. The reaction mixture was cooled to room temperature poured into water (250 mL) and extracted into EtOAc (2×100 mL). The organic layer was washed several times with water, dried over sodium sulfate, concentrated in vacuo, and the residue was purified by flash chromatography eluting with hexane: EtOAc (95:5) to yield 66.8 g of 5-(2,4-difluoro-phenoxy)-2-nitro-benzoic acid methyl ester (1A).

1B. 5-(2,4-Difluoro-phenoxy)-2-nitro-benzoic acid

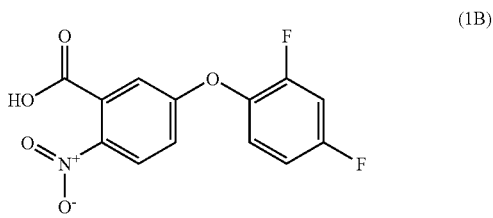

(1B)

To a solution of compound (1A) (66 g, 0.21 mol) in water/MeOH (180/180 mL) was added NaOH (27 g, 0.68 mol), and the mixture was heated to reflux for 2 h. After cooling to room temperature, the reaction was acidified with 10% HCl and extracted into EtOAc. The organic layer was washed with brine, dried over sodium sulfate, concentrated in vacuo, and crystallized from ether/ hexane to afford 53 g of 5-(2,4-difluoro-phenoxy)-2-nitro-benzoic acid (1B).

1C. 5-(2,4-Difluoro-phenoxy)-2-nitro-benzamide

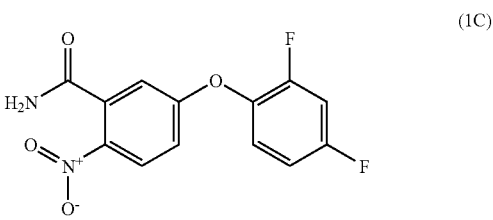

(1C)

A mixture of compound (1B) (53 g, 0.18 mol), thionyl chloride (51.3 mL) and DMF (1 mL) was stirred at room temperature for 18 h, then concentrated in vacuo to dryness. This acid chloride (60.7 g) was dissolved in THF (400 mL), and NH$_4$OH (235 mL) was added. The mixture was then stirred for 18 h and concentrated in vacuo. The residue was purified by flash chromatography eluting with hexane:EtOAc (4:1) to afford 27.7 g of 5-(2,4-difluoro-phenoxy)-2-nitro-benzamide (1C).

1D. 2-Amino-5-(2,4-difluoro-phenoxy)-benzamide

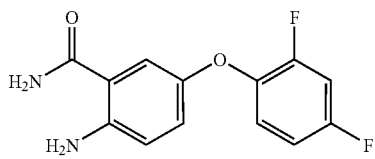

(1D)

To compound (1C) (27 g, 0.09 mol) in EtOH was added palladium on activated carbon (2.7 g), and the mixture was stirred under hydrogen for 18 h. The suspension was filtered through celite and the filtrate concentrated and dried in vacuo to yield 23 g of 2-amino-5-(2,4-difluoro-phenoxy)-benzamide (1D).

1E. 6-(2,4-Difluoro-phenoxy)-1H-quinazoline-2,4-dione

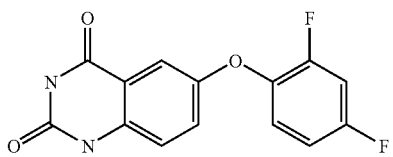

(1E)

Compound (1D) (23 g, 0.09 mol) and urea (25.42 g, 0.41 mol) in NMP (150 mL) were heated to 170° C. for 18 h. After cooling to room temperature, the reaction mixture was poured into water (200 mL) and stirred for 1 h. The precipitate was filtered, washed with water, and dried to afford 22.7 g of 6-(2,4-difluoro-phenoxy)-1H-quinazoline-2,4-dione (1E).

1F. 2,4-Dichloro-6-(2,4-difluoro-phenoxy)-quinazoline

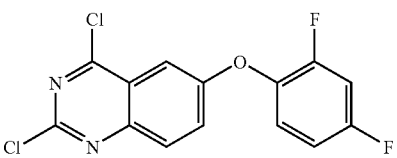

(1F)

Compound (1E) (22.6 g, 0.08 mol), N,N-diethylaniline (7.2 mL) and $POCl_3$ (248 mL) were heated at 120° C. for 4 h. After cooling to room temperature, the excess $POCl_3$ was evaporated, and the residue was made basic with 10% $NaHCO_3$ and extracted into EtOAc (2×100 mL). The combined organic layers were dried over sodium sulfate and evaporated in vacuo. The crude product was purified by chromatography (silica gel, hexane: EtOAc, 4:1) giving 21.1 g of 2,4-dichloro-6-(2,4-difluorophenoxy)-quinazoline (1F).

1G. 2-Chloro-6-(2,4-difluoro-phenoxy)-quinazolin-4-ylamine

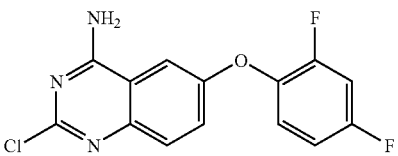

(1G)

Compound (1F) (21 g, 0.06 mol) was suspended in ammonia (100 mL of 2.0 M solution in MeOH) and the solution formed after 30 min was stirred at room temperature for 18 h. The precipitate was filtered, the concentrated filtrate triturated with EtOAc, and the organic layers were combined to yield 21.5 g of 2-chloro-6-(2,4-difluorophenoxy)-quinazolin-4-ylamine (1G).

1H. 2-Chloro-6-(2,4-difluoro-phenoxy)-quinazoline (1H)

Compound (1G) (21 g, 0.07 mol) was dissolved in THF (200 mL) and the solution added dropwise to a solution of t-butyl nitrite (16.5 mL, 0.14 mol) in THF (100 mL). The mixture was heated to reflux for 4 h, and after cooling to room temperature, the reaction mixture was poured into water and extracted with EtOAc (2×100 mL). The combined organic layers were dried over sodium sulfate and evaporated in vacuo. The crude product was purified by chromatography (silica gel, hexane: EtOAc, 4:1) giving 9.05 g of 2-chloro-6-(2,4-difluoro-phenoxy)-quinazoline (1H).

1I 2-[6-(2,4-Difluoro-phenoxy)-quinazolin-2-ylamino]-2-ethyl-propane-1,3-diol (Example 1)

Compound (1G) (250 mg, 0.85 mmol) and 2-amino-2-ethyl-1,3-propanediol (298 mg, 2.5 mmol) in NMP (0.25 mL) were stirred at 120° C. for 4 h. After cooling to room temperature, the reaction mixture was poured into water and extracted with EtOAc (2×25 mL). The combined organic layers were dried over sodium sulfate and evaporated in vacuo. The crude product was purified by chromatography (silica gel, $CH_2Cl_2$: MeOH, 95:5) to afford 150 mg of the above-titled compound (Example 1). Mp=110-112.9° C. MW $(M+H)^+=376$.

EXAMPLES 2-5

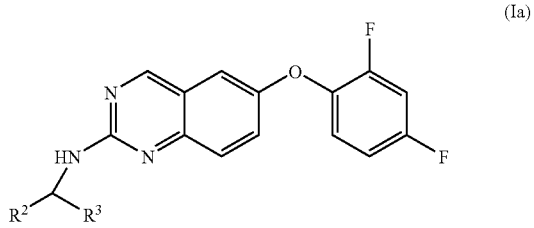

(Ia)

Compounds having the Formula I(a) above, wherein $R^2$ and $R^3$ have the values set forth in Tables 1 and 2, were prepared following the same or similar method as described above for EXAMPLE 1, except the appropriate amine was used in place of 2-amino-2-ethyl-1,3-propanediol in Step 1I.

at 120° C. for 18 h. After cooling to room temperature, the reaction mixture was poured into water and extracted with EtOAc (2×25 mL). The combined organic layers were dried over sodium sulfate and evaporated in vacuo. The crude product was purified by chromatography (silica gel, hexane:

TABLE 1

| Ex. No. | $R^2$ | $R^3$ | Compound Name | Mp (° C.) | MW |
|---|---|---|---|---|---|
| 2 | —CH$_3$ | —CH$_3$ | 6-(2,4-Difluoro-phenoxy)-quinazolin-2-yl]-(isopropyl)-amine | 160-162.6 | 315.32 |
| 3 | —CH$_2$CH$_2$OH | —CH$_2$CH$_2$OH | 3-[6-(2,4-Difluoro-phenoxy)-quinazolin-2-ylamino]-pentane-1,5-diol | 112.9-113.6 | 375.37 |

TABLE 2

| Ex. No. | $R^2$ | $R^3$ | Compound Name | Mp (° C.) | MW |
|---|---|---|---|---|---|
| 4 | —H | (2,3-dihydroxypropyl group) | 3-[6-(2,4-Difluoro-phenoxy)-phenoxy)-quinazolin-2-ylamino]-propane-1,2-diol | 161.5-162.7 | 347.32 |
| 5 | —H | (2-methanesulfonyl-ethyl group) | 6-(2,4-Difluoro-phenoxy)-quinazolin-2-yl]-(2-methanesulfonyl-ethyl)-amine | 160.1-161.5 | 379.39 |

EXAMPLE 6

6-(2,4-Difluoro-phenoxy)-quinazolin-2-yl]-(1-methanesulfonyl-piperidin-4-yl)-amine

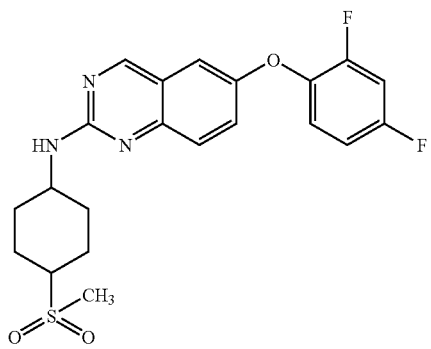

2-Chloro-6-(2,4-difluoro-phenoxy)-quinazoline (250 mg, 0.85 mmol) (compound 1I, prepared as described in Example 1, steps A-H), and 1-(methylsulfonyl) piperidin-4-amine (228 mg, 1.25 mmol) in NMP (0.25 mL) were stirred EtOAc, 1:1) to afford 105 mg of the above-titled Example 6. Mp=173.9-177.1° C., MW (M+H)$^+$=435.

EXAMPLES 7-10

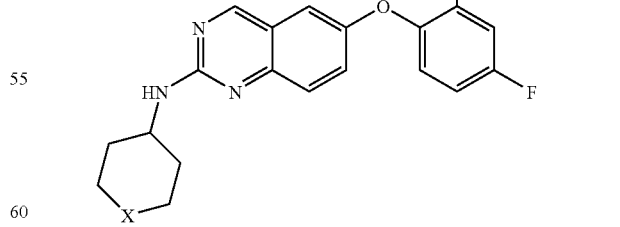

(Ib)

Compounds having the Formula (Ib) above, wherein X has the values set forth in Table 3, were prepared following the same or similar method as described above for Example 6, except the appropriately-substituted amine was used in place of 1-(methylsulfonyl)piperidin-4-amine.

TABLE 3

| Ex. No. | X | Compound Name | Mp (° C.) | MW |
|---|---|---|---|---|
| 7 | —O— | [6-(2,4-Difluoro-phenoxy)-quinazolin-2-yl]-(tetrahydro-pyran-4-yl)-amine | 179-180.9 | 357.36 |
| 8 | | 4-[6-(2,4-Difluoro-phenoxy)-quinazolin-2-ylamino]-cyclohexanol | 176.2-176.8 | 371.39 |
| 9 | | 4-[6-(2,4-Difluoro-phenoxy)-quinazolin-2-ylamino]-piperidine-1-carboxylic acid ethyl ester | 154.1-155.0 | 428.44 |
| 10 | —N(H)— | 6-(2,4-Difluoro-phenoxy)-quinazolin-2-yl]-piperidin-4-yl-amine | 163.0-165.3 | 356.37 |

EXAMPLE 11

(6-Ethoxy-quinazolin-2-yl)-(2-methanesulfinyl-ethyl)-amine

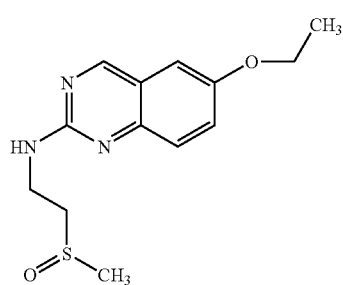

2-Chloro-6-ethoxy-quinazoline (500 mg, 2.4 mmol) and 2-methylsulfanyl-ethylamine (0.67 mL, 7.25 mmol) in NMP (0.5 mL) were stirred at 80° C. for 18 h. After cooling to room temperature, the reaction mixture was poured into water and extracted with EtOAc (2×25 mL). The combined organic layers were dried over sodium sulfate and evaporated in vacuo. The crude product was dissolved in DCM (5 mL) and cooled in an ice bath. 3-Chloroperoxybenzoic acid (911 mg, 5.2 mmol) was then added, and the reaction mixture was stirred for 5 h, diluted with EtOAc (15 mL), washed with 5% $NaHCO_3$ (10 mL), dried over sodium sulfate, and evaporated in vacuo. The crude product was purified by chromatography (silica gel, first EtOAc 100%, then $CH_2Cl_2$:MeOH [95:5]) to afford 250 mg of the above titled Example 11. Mp=152.7-154.6° C., MW $(M+H)^+$=280.

EXAMPLES 12-15

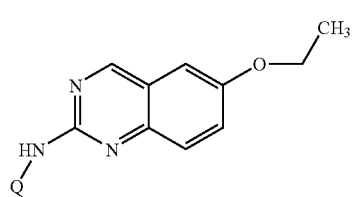

II(a)

Compounds having the Formula II(a) above, wherein Q has the values set forth in Table 4, were prepared following the same or similar method as described above for Example 11, except the appropriate amine was used in place of 2-methylsulfanyl-ethylamine.

TABLE 4

| Ex. No. | X | Compound Name | Mp (° C.) | MW |
|---|---|---|---|---|
| 12 | | 3-(6-Ethoxy-quinazolin-2-ylamino)-pentane-1,5-diol | | 291 |
| 13 | | (6-Ethoxy-quinazolin-2-yl)-(1-methanesulfonyl-piperidin-4-yl)-amine | 168.0–173 | 350.44 |
| 14 | | 4-(6-Ethoxy-quinazolin-2-ylamino)-piperidine-1-carboxylic acid ethyl ester | 164.4–165.0 | 345 |
| 15 | | (6-Ethoxy-quinazolin-2-yl)-(2-methanesulfonyl-ethyl)-amine | | 296 |

EXAMPLE 16

The following are representative pharmaceutical formulations containing a compound of (I) or (II).

Tablet Formulation

The following ingredients are mixed intimately and pressed into single scored tablets.

| Ingredient tablet, mg | Quantity per |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient capsule, mg | Quantity per |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| Sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
| --- | --- |
| compound of this invention | 0.2 g |
| sodium acetate buffer solution, 0.4 M | 2.0 ml |
| HCl (1N) or NaOH (1N) | q.s. to suitable pH |
| water (distilled, sterile) | q.s. to 20 ml |

All of the above ingredients, except water, are combined and heated to 60-70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| compound of the invention | 500 mg |
| --- | --- |
| Witepsol ® H-15 | balance |

EXAMPLE 17

Inhibition of p-38 (MAP) Kinase-In Vitro Assay

The p-38 MAP kinase inhibitory activity of compounds of this invention in vitro was determined by measuring the transfer of the γ-phosphate from γ-$^{33}$P-ATP by p-38 kinase to Myelin Basic Protein (MBP), using the a minor modification of the method described in Ahn et al., *J. of Biol. Chem.*, Vol. 266 (7), 4220-4227 (1991).

The phosphorylated form of the recombinant p38 MAP kinase was expressed with SEK-1 and MEKK in *E. Coli* (see Khokhlatchev et al., *J. of Biol. Chem.* Vol. 272(17), at pp. 11057-11062 (1997)), and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis(beta-aminoethyl ether)-N,N,N',N'-tetraacetic acid, 1 mM sodium vanadate, 1 mM dithiothreitol, 40 mM magnesium chloride). Test compound dissolved in DMSO or only DMSO (control) was added, and the samples were incubated for 10 min. at 30° C. The kinase reaction was initiated by the addition of a substrate cocktail containing MBP and γ-$^{33}$P-ATP. After incubating for an additional 20 min. at 30° C., the reaction was terminated by adding 0.75% phosphoric acid. The phosphorylated MBP was then separated from the residual γ-$^{33}$P-ATP using a phosphocellulose membrane (Millipore, Bedfrod, Mass.) and quantitated using a scintillation counter (Packard, Meriden, Conn.).

The compounds described in the Examples herein were tested in the above assay and found to have a measurable level of p38 inhibitory activity. As an illustration, Table 5 below lists approximate p38 inhibitory activities of certain compounds according to the invention (expressed as IC$_{50}$, the concentration causing 50% inhibition of the p38 enzyme being analyzed).

TABLE 5

| Ex. No. | IC$_{50}$ |
| --- | --- |
| 1 | <.10 |
| 2 | <.03 |
| 4 | <2 |
| 5 | ≈2 |
| 6 | <.001 |
| 8 | <.03 |
| 12 | >10 |

The foregoing discussion of the invention has been presented for purposes of illustration and description. The foregoing is not intended to limit the invention to the forms disclosed herein. Although the description of the invention has included one or more embodiments and certain variations and modifications, other variations and modifications are within the scope of the invention, e.g., as may be within the skill and knowledge of those in the art. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All publications, patents, and patent applications cited herein are hereby incorporated by reference in their entirety.

The invention claimed is:

1. A compound having the Formula (I):

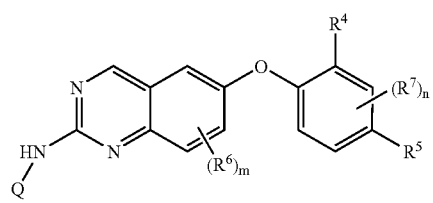

or an isomer, prodrug, or pharmaceutically-acceptable salt thereof, wherein:

Q is —C(R$^1$R$^2$R$^3$);

R$^1$ is selected from hydrogen, alkyl, hydroxyalkyl, and alkoxyalkyl;

R$^2$ and R$^3$ are selected:
  (i) independently from:
    (a) hydrogen, provided if R$^1$ is hydrogen, only one of R$^2$ and R$^3$ may be selected from hydrogen;
    (b) alkyl;

(c) alkyl substituted with one, two, or three of halogen, cyano, —OR$^8$, —SR$^8$, —C(=O)R$^8$, —C(O)$_2$R$^8$, —C(=O)NR$^8$R$^9$, —S(O)$_p$R$^{10}$, —C(O)$_2$NR$^8$R$^9$, —S(O)$_2$NR$^8$R$^9$, and/or —NR$^8$R$^9$;

(d) —OR$^3$, —SR$^8$, —C(=O)R$^8$, —C(O)$_2$R$^8$, —C(=O)NR$^8$R$^9$, —S(O)$_p$R$^{10}$, —C(O)$_2$NR$^8$R$^9$, and —S(O)$_2$NR$^8$R$^9$;

(e) cycloalkyl, substituted cycloalkyl, heterocyclyl, substituted heterocyclyl, cycloalkylalkyl, substituted cycloalkylalkyl, heterocycloalkyl, and substituted heterocycloalkyl;

or alternatively, (ii) R$^2$ and R$^3$ are taken together to form an optionally-substituted cycloalkyl or heterocyclyl ring;

R$^4$ and R$^5$ are independently selected from hydrogen, halogen, cyano, haloalkyl, and haloalkoxy, provided R$^4$ and R$^5$ are not both hydrogen;

R$^6$ may be attached to carbon atoms C5, C7, and/or C8 of the quinazoline ring, and when attached to carbon atom C5 is lower alkyl and when attached to C7 and/or C8 is independently selected from alkyl, halogen, cyano, nitro, hydroxy, alkoxy, haloalkoxy, amino, alkylamino, and alkyl substituted with one to two of halogen, cyano, nitro, hydroxy, alkoxy, haloalkoxy, amino, and/or alkylamino;

R$^7$ is attached to any available carbon atom of the phenyl ring and at each occurrence is independently selected from alkyl, substituted alkyl, halogen, cyano, nitro, hydroxy, alkoxy, haloalkoxy, amino, and alkylamino;

R$^8$ and R$^9$ are (i) independently selected from hydrogen, alkyl, haloalkyl, hydroxyalkyl, alkoxyalkyl, cycloalkyl, substituted cycloalkyl, heterocyclyl, and substituted heterocyclyl; or (ii) when R$^8$ and R$^9$ are attached to the same nitrogen atom (as in —C(O)$_2$NR$^8$R$^9$, —S(O)$_2$NR$^8$R$^9$, and —NR$^8$R$^9$), R$^8$ and R$^9$ may be taken together to form an optionally-substituted heterocyclyl ring;

R$^{10}$ is alkyl, hydroxyalkyl, alkoxyalkyl, cycloalkyl, substituted cycloalkyl, heterocyclyl, or substituted heterocyclyl;

m is 0, 1, 2 or 3;

n is 0, 1 or 2; and p is 1 or 2.

2. A compound according to claim 1, or an isomer, prodrug, or pharmaceutically-acceptable salt thereof, wherein:

R$^1$ is selected from hydrogen and $C_{1-4}$alkyl;

R$^2$ and R$^3$ are (i) independently selected from $C_{1-6}$alkyl and $C_{1-6}$alkyl substituted with one to two of hydroxy, —O($C_{1-4}$alkyl), —C(O)$_2$($C_{1-4}$alkyl), and/or —S(O)$_p$($C_{1-4}$alkyl); or (ii) R$^2$ and R$^3$ taken together form a $C_{3-7}$cycloalkyl or a five to six membered monocyclic heterocyclic ring, wherein each of said rings is optionally-substituted with 0 to 1 of R$^{12}$ and/or 0 to 1 of R$^{14}$;

R$^4$ and R$^5$ are both halogen;

R$^{12}$ and R$^{14}$ are independently selected from $C_{1-4}$alkyl, hydroxy, oxo (=O), —O($C_{1-4}$alkyl), —C(=O)H, —C(=O)($C_{1-4}$alkyl), —C(O)$_2$H, —C(O)$_2$($C_{1-4}$alkyl), and —S(O)$_2$($C_{1-4}$alkyl);

m is 0; and n is 0.

3. A compound according to claim 1, or an isomer, prodrug, or pharmaceutically-acceptable salt thereof, wherein R$^1$ is selected from hydrogen and $C_{1-4}$alkyl.

4. A compound according to claim 1, or an isomer, prodrug, or pharmaceutically-acceptable salt thereof, wherein m and n are both 0.

5. A compound according to claim 1, or an isomer, prodrug, or pharmaceutically-acceptable salt thereof, wherein:

R$^2$ and R$^3$ are selected (i) independently from:

1) alkyl substituted with one or two of halogen, cyano, —OR$^8$, —SR$^8$, —C(=O)R$^8$, —C(O)$_2$R$^8$, —C(=O)NR$^8$R$^9$, —S(O)$_p$R$^{10}$, —C(O)$_2$NR$^8$R$^9$, —S(O)$_2$NR$^8$R$^9$, and/or —NR$^8$R$^9$, 2) —S(O)$_p$R$^{10}$, —C(O)$_2$NR$^8$R$^9$, or —S(O)$_2$NR$^8$R$^9$; and 3) cycloalkyl, substituted cycloalkyl, heterocyclyl, substituted heterocyclyl, cycloalkylalkyl, substituted cycloalkylalkyl, heterocycloalkyl, and substituted heterocycloalkyl;

or alternatively, (ii) R$^2$ and R$^3$ are taken together to form an optionally-substituted cycloalkyl or heterocyclyl ring.

6. A compound according to claim 1, or an isomer, prodrug, or pharmaceutically-acceptable salt thereof, wherein:

R$^2$ and R$^3$ are independently selected from hydrogen, $C_{1-6}$alkyl, and hydroxy($C_{1-6}$alkyl).

7. A compound according to claim 1, or an isomer, prodrug, or pharmaceutically-acceptable salt thereof, wherein:

R$^2$ and R$^3$ are taken together to form an optionally-substituted $C_{3-7}$cycloalkyl or an optionally-substituted heterocyclic ring.

8. A compound according to claim 1, or an isomer, prodrug, or pharmaceutically-acceptable salt thereof, wherein:

R$^2$ and R$^3$ are (i) independently selected from hydrogen, $C_{1-4}$alkyl, and hydroxy($C_{1-4}$alkyl), provided R$^2$ and R$^3$ are not both hydrogen; or (ii) R$^2$ and R$^3$ are taken together to form cyclohexyl, piperidin-4-yl, or tetrahydropyran-4-yl, wherein each of said rings formed by R$^2$ and R$^3$ taken together is optionally-substituted with up to two of lower alkyl, —OH, —C(O)$_2$($C_{1-4}$alkyl) and/or —S(O)$_2$(CH$_3$).

9. A compound according to claim 1, or an isomer, prodrug, or pharmaceutically-acceptable salt thereof, wherein R$^4$ and R$^5$ are both halogen.

10. A compound according to claim 1, or an isomer, prodrug, or pharmaceutically-acceptable salt thereof, having the formula:

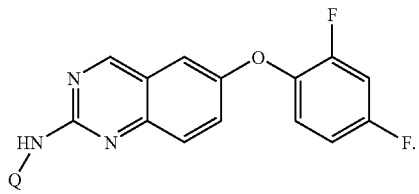

11. A compound according to claim 1, or an isomer, prodrug, or pharmaceutically-acceptable salt thereof, having the formula:

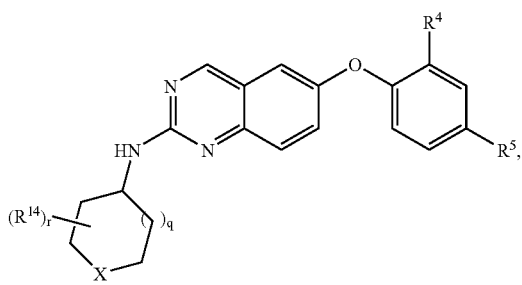

wherein:
X is —O—, —C(=O)—, —N($R^{12a}$)—, or —CH($R^{12b}$)—;
$R^{12a}$ is selected from hydrogen, $C_{1-4}$alkyl, —C(=O)$R^{15}$, —C(O)$_2R^{15}$, and —S(O)$_2$($C_{1-4}$alkyl);
$R^{12b}$ is selected from hydrogen, $C_{1-4}$alkyl, —O$R^{15}$, —C(=O)$R^{15}$, —C(O)$_2R^{15}$, and —S(O)$_2$($C_{1-4}$alkyl);
$R^{14}$ is selected from $C_{1-4}$alkyl, oxo (=O), —O$R^{15}$, —C(=O)$R^{15}$, —C(O)$_2R^{15}$, and —S(O)$_2$($C_{1-4}$alkyl);
$R^{15}$ at each occurrence is independently selected from hydrogen and $C_{1-4}$alkyl;
q is 0 or 1; and
r is 0, 1, or 2.

12. A compound according to claim 11, or an isomer, prodrug, or pharmaceutically-acceptable salt thereof, wherein:
$R^4$ and $R^5$ are both fluoro.

13. A compound according to claim 11, or an isomer, prodrug, or pharmaceutically-acceptable salt thereof, wherein X is —$NR^{12a}$—, $R^{12a}$ is —S(O)$_2$($C_{1-4}$alkyl), and q is 1.

14. A compound having the Formula (Ip),

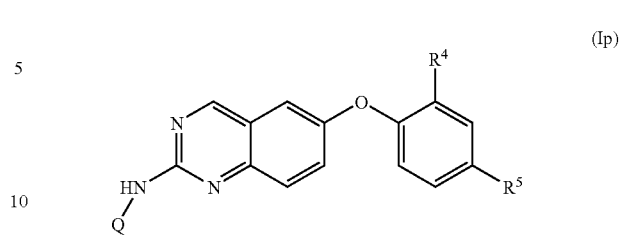

or an isomer, prodrug, or pharmaceutically-acceptable salt thereof, wherein:
Q is —C($R^1R^2R^3$) or an optionally-substituted cycloalkyl or heterocyclyl;
$R^1$ is selected from hydrogen and alkyl;
$R^2$ and $R^3$ are independently selected from —Y—$R^8$, —Y—O$R^8$, —Y—S$R^8$, —Y—S(O)$_pR^{10}$, —Y—C(=O)$R^8$, and —Y—C(O)$_2R^8$, wherein Y is $C_{1-6}$alkylene;
$R^4$ and $R^5$ are both halogen;
$R^8$ is selected from hydrogen, alkyl, substituted alkyl, cycloalkyl, substituted cycloalkyl, heterocyclyl, and substituted heterocyclyl, provided $R^8$ is not arylalkyl or heteroarylalkyl;
$R^{10}$ is alkyl, substituted alkyl, cycloalkyl, substituted cycloalkyl, heterocyclyl, or substituted heterocyclyl, provided $R^{10}$ is not arylalkyl or heteroarylalkyl; and
p is 1 or 2.

15. A compound according to claim 14, or an isomer, prodrug, or pharmaceutically-acceptable salt thereof, wherein $R^4$ and $R^5$ are both fluoro.

16. A compound according to claim 14, or an isomer, prodrug, or pharmaceutically-acceptable salt thereof, wherein at least one of $R^2$ and $R^3$ is selected from —Y—O$R^8$, —Y—S(O)$_pR^{10}$, —Y—C(=O)$R^8$, and —Y—C(O)$_2R^8$, wherein Y is $C_{1-4}$alkylene.

17. A compound according to claim 14, or an isomer, prodrug, or pharmaceutically-acceptable salt thereof, wherein Q is an optionally-substituted monocyclic cycloalkyl or heterocyclyl ring.

18. A pharmaceutical composition comprising a therapeutically effective amount of compound according to claim 1 in combination with a pharmaceutically-acceptable excipient.

* * * * *